US006730019B2

(12) United States Patent
Irion

(10) Patent No.: US 6,730,019 B2
(45) Date of Patent: May 4, 2004

(54) ENDOSCOPE WITH LED ILLUMINATION

(75) Inventor: Klaus M. Irion, Liptingen (DE)

(73) Assignee: Karl Storz GmbH & Co. KG (DE)

( * ) Notice: Subject to any disclaimer, the term of this patent is extended or adjusted under 35 U.S.C. 154(b) by 258 days.

(21) Appl. No.: 10/033,441

(22) Filed: Oct. 24, 2001

(65) Prior Publication Data

US 2002/0120181 A1 Aug. 29, 2002

(30) Foreign Application Priority Data

Oct. 24, 2000 (DE) ..................................... 200 18 213 U
Oct. 24, 2000 (EP) ............................................ 00123081

(51) Int. Cl.[7] ................................................. A61B 1/06
(52) U.S. Cl. ....................... 600/178; 362/555; 362/574; 600/182
(58) Field of Search ................................ 600/101, 178, 600/179, 182; 362/554, 555, 572, 574

(56) References Cited

U.S. PATENT DOCUMENTS 5,241,170 A    8/1993  Field, Jr. et al. ............ 250/214
6,318,887 B1 * 11/2001  Matsumoto .................. 362/574
6,331,156 B1 * 12/2001  Haefele et al. .............. 600/179
6,449,006 B1 *  9/2002  Shipp .......................... 348/70

FOREIGN PATENT DOCUMENTS

| DE | 94 02 678    | 5/1994  |
| DE | 94 02 678 U1 | 5/1994  |
| DE | 197 15 510   | 10/1998 |
| DE | 299 22 755   | 4/2000  |
| EP | 0 557 709    | 9/1993  |
| WO | WO98/02085   | 1/1998  |
| WO | WO00/54655   | 9/2000  |

* cited by examiner

*Primary Examiner*—Michael Peffley
(74) *Attorney, Agent, or Firm*—St. Onge Steward Johnston & Reens LLC

(57) ABSTRACT

An endoscope comprising a shaft comprises an imaging system arranged in the shaft and an illuminating system which allows light emitted by a light source to emerge at the distal end of shaft, wherein the light source comprises at least one light emitting diode. The light source comprises at least two light emitting diodes which emit light in different spectral ranges, and the light of the at least two light emitting diodes emerges spectrally additively mixed from the illuminating system.

17 Claims, 3 Drawing Sheets

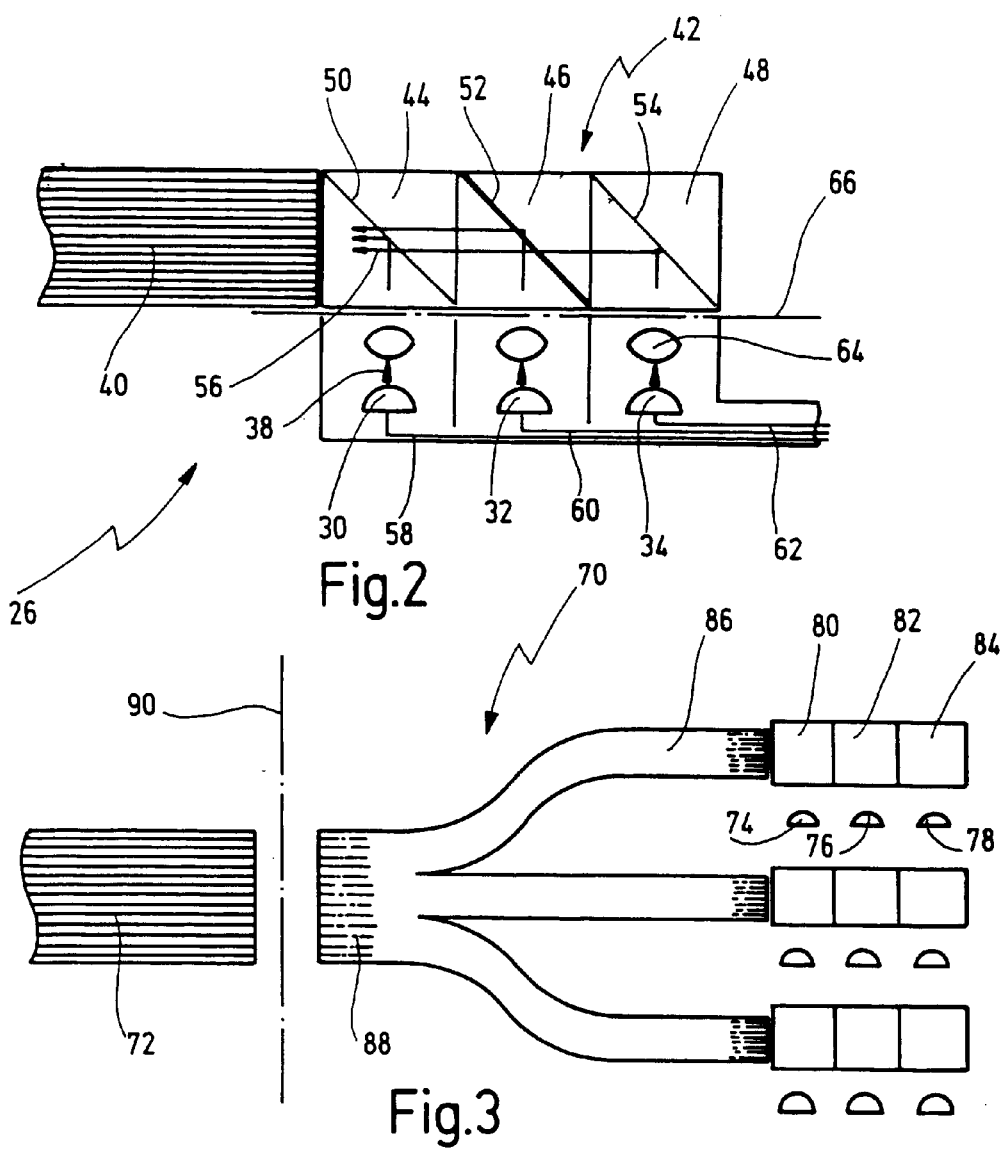
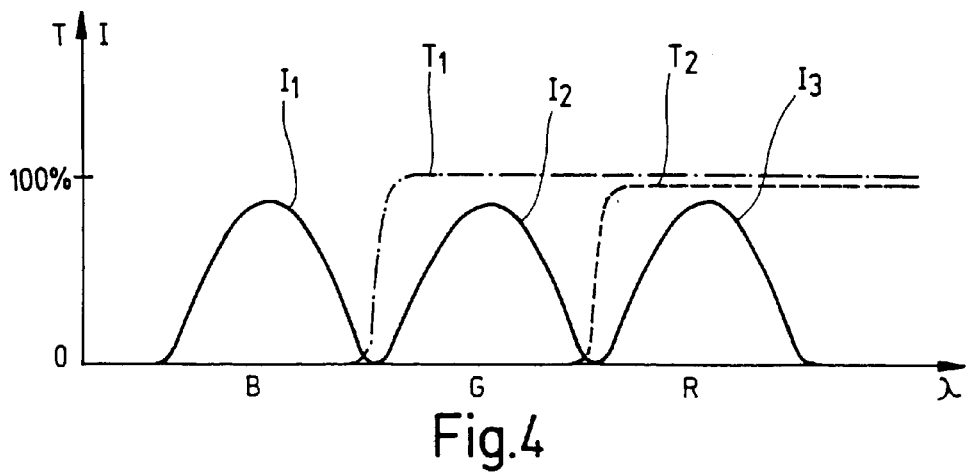

ENDOSCOPE WITH LED ILLUMINATION

BACKGROUND OF THE INVENTION

The invention relates to an endoscope, comprising a shaft, an imaging system arranged in the shaft, and an illuminating system which allows light emitted by a light source to emerge at the distal end of the shaft, wherein the light source comprises at least one light emitting diode.

Such an endoscope is known from the German utility model 299 22 755.

Endoscopes are used both in the technical field and in the medical field.

Examples of application of a technical endoscope are the inspection of difficultly accessible cavities in machines, motors, turbines, reaction spaces etc. which are, thus, not observable with the naked eye.

In medical endoscopy, endoscopes are used in minimal-invasive surgery, if necessary, in combination with surgical instruments for purposes of examination or for operations with visual control or for application of diagnostic or therapeutic light.

A first component of such endoscopes is the imaging system. The imaging system serves for receiving observation light from the observation space or the operation space, respectively, and for transmitting image information from distally to proximally.

The imaging system may, conventionally, consist in an optical image transmission system which comprises an objective in the distal end of the shaft, a lens system proximally adjoining to same, e.g. in the form of rod lenses, or an ordered fiber bundle and a proximal eyepiece, by which it is possible to observe with the eye, or onto which a camera can be connected.

The imaging system may, however, in the distal end of the shaft, also comprise a camera module with an imaging optic and an imager chip, e.g. in the form of a CCD-chip which transforms the light signals into electric signals which are transmitted to proximal via electric lines and which are visually presented, as a real image, on an image reproduction unit outside the endoscope.

A second component of such endoscopes the present invention refers to is the illuminating system. The illuminating system serves for transmitting light from proximally to distally in order to illuminate the observation space or the examination space, respectively, with light. For a bright illumination, white light is usually used, whereas for other applications, e.g. examinations with excitation light, colored light is also used.

For endoscopes used at present, the illuminating system comprises an external light source, commonly on the basis of a xenon or halogen lamp. The endoscope is then connected with the external light source via a light conducting cable.

Apart from that such xenon or halogen light sources are very cost-intensive apparatus, another disadvantage of such common endoscopes is that the connection of the endoscope with the light source via a light conducting cable is disturbing during the use of the endoscope. Due to the long transmission path from the light source to the distal tip of the endoscope that can be 2 through 3 m, besides, losses in the light intensity of the light emerging from the distal end of the endoscope may occur which have to be balanced by a suitably luminous light source with a corresponding cost effort.

The endoscope known from the utility model mentioned above does not operate with an external light source by integrating at least one light emitting diode (LED) in the endoscope. As light emitting diodes are, in the meanwhile, available with a high light intensity, the observation space or the examination space can be illuminated sufficiently brightly with a light emitting diode as light source. Thus, an external cost-intensive light source can be saved. In addition, light emitting diodes have the advantage in the case of the application of colored light, that the color quality of the light of an LED is better than if a white light source with a color filter is used. Moreover, the light conducting cable which would be disturbing during the applications of the endoscope between the external light source and the endoscope becomes superfluous, whereby, on the one hand, further costs are saved, and, on the other hand, the handling of the endoscope is improved.

Light emitting diodes would be generally suitable for the application in endoscopy due to their structural shape and their efficiency, both for a continuous and for a pulsed illumination. The disadvantage of light emitting diodes, however, is that the power density of the light emitted by light emitting diodes is not very high and that light emitting diodes that are stronger in power radiate in a relatively narrow-band. For example, diodes exist that are stronger in power and that radiate in a narrow band particularly in the red and infrared region. In comparison to that, there are requirements in the endoscopy that always faithfully colored images and no "one color" (e.g. red) or black-and-white images, respectively, are required.

It is therefore the object of the present invention to improve an endoscope of the type mentioned at the outset such that as faithfully colored images as possible can be observed through the endoscope.

SUMMARY OF THE INVENTION

According to the invention, this object is achieved by an endoscope, comprising:
a shaft having a distal end and a proximal end;
an imaging system arranged in said shaft;
a light source;
an illuminating system allowing light emitted by said light source to emerge at said distal end of said shaft,
wherein said light source comprises at least two light emitting diodes which emit light in different spectral ranges, and wherein said light of said at least two light emitting diodes emerges spectrally additively mixed from said illuminating system.

By means of the additive color mixture of the light of at least two light emitting diodes provided according to the invention, an endoscopic image as faithful as possible with respect to the colors of the image is achieved because it is possible due to the invention to mix the light of two spectrally narrow band light emitting diodes such that it results in white light by an additive mixture of colors. If the examination space or the observation space, respectively, is illuminated with white light, a faithful endoscopic image with respect to the colors of the image can be achieved. This measure allows it, in particular, to use high power light emitting diodes, wherein their naturally spectral narrow-bandness ("monochromatic") by the additive mixture of light emitted by the LED's can be balanced in order to achieve a faithful endoscopic image with respect to the colors of the image. Furthermore, the effect is used that the light intensities of the at least two LED's are added to a high light intensity.

To this end, it is particularly preferred if the at least two light emitting diodes emit light in spectral regions that are spectrally complementary to each other.

By this measure, due to the additive color mixture of the light emitted by the at least two light emitting diodes, exact white light of high light intensity is generated. For example, a light emitting diode having a maximal radiation power in the frequency range of the spectral color blue together with a light emitting diode having a maximal radiation power in the spectral range of the color orange, or, for instance, a light emitting diode radiating in the red spectral range can be used together with a light emitting diode radiating in the green spectral range.

In another preferred embodiment, the light source comprises at least three light emitting diodes which emit light preferably in the blue, green, and red spectral region.

Such a light emitting diode arrangement comprising at least three light emitting diodes in the blue, green, and red spectral range does not only offer advantageously the possibility of generating white light that is even stronger in intensity, but also offers the possibility of a modulation in color and/or intensity with corresponding well-aimed drive of the three individual light emitting diodes and a corresponding mixture of the light emitted by the individual light emitting diodes.

In another preferred embodiment, the at least two light emitting diodes are light emitting diodes comprising a spectrally narrow-band radiation characteristic and a high light intensity, in particular are high-brightness or ultrahigh-brightness light emitting diodes.

Such HB or UHB LED's, respectively, that are available today, which are produced on the basis of semiconductor compounds like GaN, ZnSe or SiC, have advantageously a very high light intensity and an excellent color quality with a spectrally narrow-band radiation characteristic. The narrow-band radiation characteristic of the individual light emitting diodes can be advantageous in certain applications in which it should be worked with colored light of high color quality, or, for example, in a therapeutic application of light in the photodynamic therapy. In connection with the additive color mixture of the light of different LED's, such LED's have the advantage that white light can be generated with high light intensity.

In another preferred embodiment, the illuminating system comprises an optical waveguide and light coupling means are provided for coupling the light emitted by the at least two light emitting diodes into the optical waveguide.

The light coupling means are an advantageous measure for coupling light, in particular from several light emitting diodes, into the same optical waveguide and, thus, to achieve the possibility of an additive color mixture of the light emitted by the individual light emitting diodes as mentioned above.

It is preferred herein if the at least two light emitting diodes and the light coupling means are arranged at the proximal end of the optical waveguide.

The arrangement of the at least two light emitting diodes and of the coupling means at the proximal end of the optical waveguide and, thus, at the proximal end of the endoscope has the advantage that, as at the proximal end of the endoscope more construction space is available than at its distal end, the endoscope according to the invention can be configured in a very narrowly constructed manner, which is required in particular for endoscopic applications in the medical field in minimal-invasive surgery.

In another preferred embodiment, the light coupling means are configured as beam splitters which comprise at least partly reflecting layers, wherein a beam splitter is assigned to each light emitting diode.

This measure is an advantageous possibility, in the case of an arrangement of several light emitting diodes, to couple the light emitted by the latter into the same optical waveguide inlet cross diameter, without that the LED's need to be necessarily arranged in a straight extension of the optical waveguide, but that the light emitting diodes can also be arranged at the side of the optical waveguide in a space-saving manner.

It is preferred herein if the beam splitters are arranged in a row in axial extension of the optical waveguide and that each beam splitter is reflecting in the spectral range of the light emitted by the assigned light emitting diode and permeable in the spectral range(s) of the light emitted by the light emitting diodes disposed therebehind.

By arranging the beam splitters in a row in an axial extension of the optical waveguide, the light emitted by the LED's can advantageously be coupled in parallel with respect to the optical waveguide axis, whereby losses in reflection are kept low in the light propagation in the optical waveguide. By the configuration of the beam splitters which are permeable in certain spectral ranges and reflecting in certain spectral ranges, the advantage is achieved that several beam splitters/light emitting diode arrangements, e.g. three beam splitters/light emitting diode arrangements for a blue, green, and red light emitting diode can be mounted in a row. By mounting several partly permeable beam splitters in a row, the further advantage is achieved that the optical waveguide cross section itself can be kept very small, what is desired in endoscopy.

In another preferred embodiment, the cross section of each beam splitter corresponds to the active cross section of the optical waveguide.

This embodiment is particularly advantageous for endoscopic applications since it allows to couple light of high power density into a small optical waveguide cross section and, in doing so, to use optimally the whole optical waveguide cross section for light transmission.

In another preferred embodiment, a plurality of arrangements of several light emitting diodes and beam splitters is provided, and a further optical waveguide is assigned to each of these arrangements, and the further optical waveguides are coupled with the first optical waveguide.

By this arrangement, the variability of the endoscope concerning the variation in color and/or the modification in intensity is further increased, apart from that, the light intensity and, thus, the brightness of the illumination of the observation space or of the operation space, respectively, can be even further improved.

In another preferred embodiment, the at least two light emitting diodes and/or, if necessary, the light coupling means are arranged in the endoscope.

It is herein advantageous that the endoscope configured like that with the integrated light source, consisting of at least two light emitting diodes and, if necessary, the light coupling means, forms as a whole an autonomous unit, which is independent of external light sources.

In another preferred embodiment, the at least one light emitting diode and/or, if necessary, the light coupling means are detachable from the endoscope.

This measure has the advantage that the one or several light emitting diodes, respectively, can be exchanged against other light emitting diodes held ready. The light coupling means in the form of the beam splitters mentioned above may be firmly integrated in the endoscope. However, the light coupling means can also be such configured that they are detachable from the endoscope.

In another preferred embodiment, the at least two light emitting diodes can be driven in pulsed or continuous manner.

The pulsed driving of the at least one light emitting diode is particularly advantageous with respect to the generation of stroboscope effects, e.g. for stroboscopy for examining the vocal cord functions. The pulsed driving can also be performed in combination with an endoscopic camera, so that several pulses of diodes of different spectral compositions can be used per beam splitter-light emitting diode arrangement, and, in that way, a modulation in color and intensity can be reached. In that manner, there is a possibility of optimizing the faithfulness of color and/or the intensity.

It is preferred herein if light emitting diodes having different radiation spectrums can be driven differently.

In that way, the modulation in color mentioned above can be achieved.

In another preferred embodiment, a drive circuit for the at least two light emitting diodes is arranged in the endoscope.

By this measure, the endoscope is advantageously an autonomous assembly and does not require an external drive circuit with disturbing connection cables for driving the at least two light emitting diodes.

It is also preferred if a current supply for the at least two light emitting diodes is arranged in the endoscope.

In that way, the endoscope according to the invention is made autonomous of external supplies. For example, the at least two light emitting diodes may be operated via a battery or via an accumulator which is e.g. arranged in the hand piece of the endoscope.

It is preferred herein if the current supply is, together with the at least two light emitting diodes, detachable as a unit from the endoscope.

It is herein advantageous that the unit of current supply and the at least two light emitting diodes, if necessary, with the light coupling means, can also be used independently of the endoscope and autonomously as a light source.

In another preferred embodiment, the at least two light emitting diodes and/or, if necessary, the light coupling means are arranged in a coupling unit that is detachable from the endoscope for light and image transmitting connection of the endoscope with a camera module.

This measure, too, is an advantageous embodiment of the endoscope, in which the at least two light emitting diodes and/or, if necessary, the light coupling means are not directly arranged in the endoscope itself, but in a coupling unit that is detachable from the endoscope which serves for light and image transmitting connection of the endoscope with a camera module. Such a coupling unit is described in DE 197 15 510 A1, the disclosure of which is herewith incorporated by reference into the present application. Different from the coupling unit described therein, the light conducting cable provided at the proximal end of the coupling unit for connection with an external light source can be omitted in the endoscope according to the invention after integration of the at least two light emitting diodes, as an external light source is now not required any more.

If, as indicated in another preferred embodiment, even the current supply for the at least two light emitting diodes is arranged in the coupling unit, the coupling unit is completely autonomous with respect to light generation and light emission. As current supply, rechargeable batteries may be received in the coupling unit, the batteries being chargeable via a suitable battery charger that is preferably directly connectable onto the coupling unit via contacts.

An even greater autonomy of the coupling unit and, thus, of the endoscope is achieved by another embodiment, in which in the coupling unit a sender is arranged for wireless transmission of a video image picked up by the camera module.

Whereas in the coupling unit described in DE 197 15 510 A1, a suitable electric cable is provided at the proximal end of the coupling unit for the image transmission, also this cable can be omitted due to the embodiment described above, whereby the coupling unit can be configured without any cable at all, together with the embodiment of the autonomous current supply described above, and, thus, the handling of the endoscope with the coupling unit is not impeded by cables. At least, however, even without the sender unit described above, the light conducting cable for connecting the coupling unit onto a light source and which usually more disturbs can be omitted by means of the present invention.

Further features and advantages can be taken from the following description of the enclosed drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

Embodiments of the invention are shown in the drawings and will be explained in more detail in the description below. In the drawings:

FIG. 2 shows a schematic view of a portion of the illuminating system of the endoscope in FIG. 1;

FIG. 3 shows a portion of an illuminating system for the endoscope in FIG. 1 according to another embodiment;

FIG. 4 shows a schematic view of the intensity distribution of the individual light emitting diodes of the endoscope in FIG. 1 and of the reflection and transmission characteristics of beam splitters for coupling the light emitted by the light emitting diodes into the optical waveguide of the endoscope in FIG. 1.

DETAILED DESCRIPTION OF PREFERRED EMBODIMENTS

Figure 1:
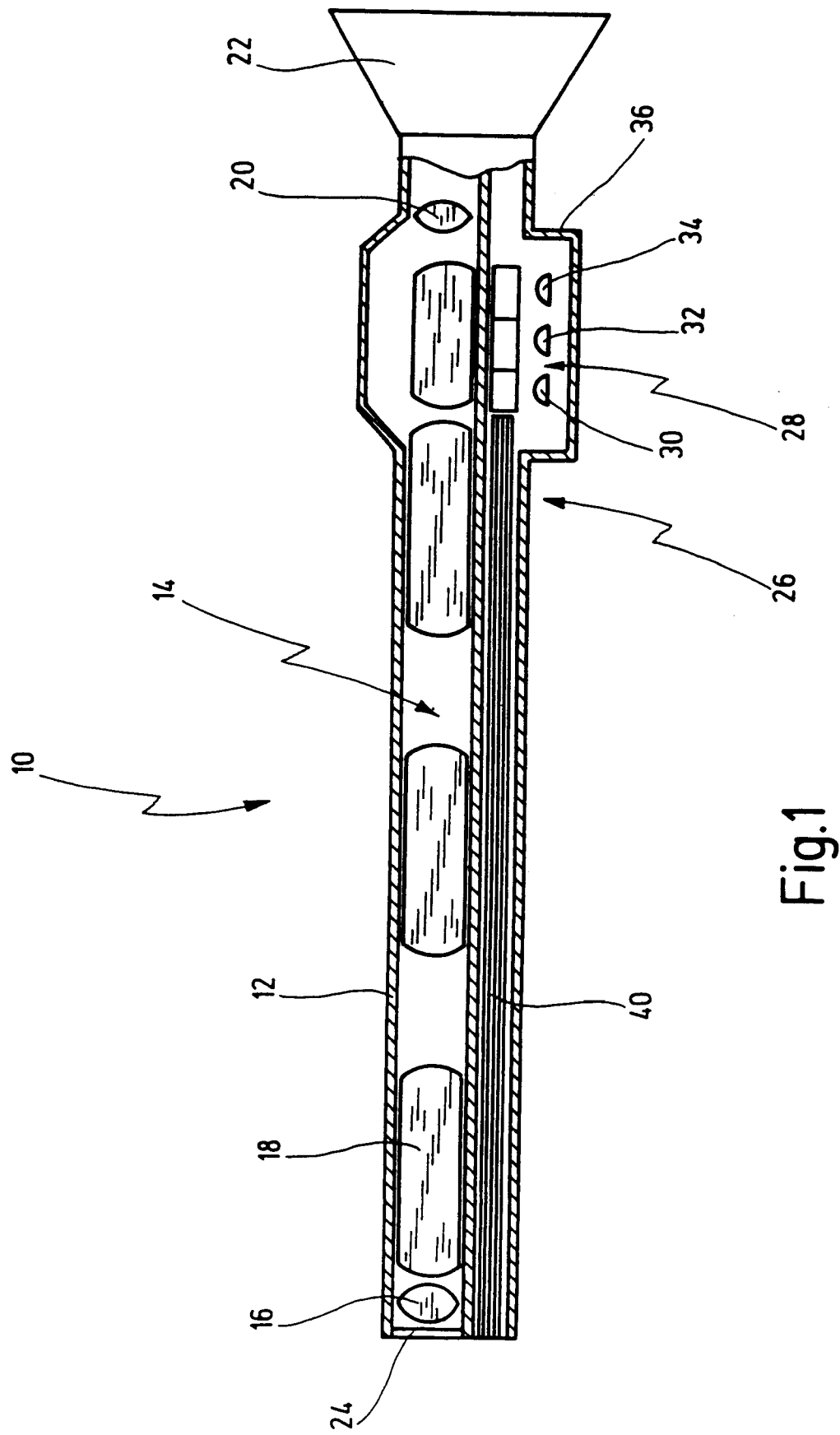
FIG. 1 shows a schematic view of an endoscope in a longitudinal section.

In FIG. 1, an endoscope designated with the general reference numeral 10 is schematically represented.

Endoscope 10 is a medical endoscope, wherein the invention is, however, not limited to medical endoscopes, but can also be applied in technical endoscopes.

Endoscope 10 comprises a shaft 12.

In shaft 12, an imaging system 14 is arranged which comprises an objective 16 in the region of the distal end of shaft 12, a lens system 18 in the form of a plurality of rod lens and eyepiece optics 20. Imaging system 14 may, however, also comprise an ordered fiber bundle or a camera module with an optoelectronic image pick-up device at the distal end of shaft 12.

An eyepiece cup 22 is arranged at the proximal end of shaft 12.

A cover glass 24 is arranged at the distal end of shaft 12.

The endoscope further comprises an illuminating system 26. Illuminating system 26 comprises a light source 28 which is configured in the form of three light emitting diodes, a first light emitting diode 30, a second light emitting diode 32 and a third light emitting diode 34 in endoscope 10.

Light emitting diodes 30, 32 and 34 are arranged at the proximal end of endoscope 10, namely within an endoscope housing 36 arranged at shaft 12.

Light emitting diodes 30, 32 and 34 are preferably so-called high brightness or ultrahigh brightness light emitting diodes (HB LED's or UHB LED's, respectively), preferably on the basis of a material compound with semiconductor characteristics.

Such a material compound with semiconductor characteristics is GaN.

However, light emitting diodes 30, 32 and 34 can also be light emitting diodes on the basis of silicon.

Furthermore, light emitting diodes on the basis of an organic semiconductor material (OLED), e.g. on the basis of poly-phenylene-vinyl (PPV) are adapted as light emitting diodes 30, 32 and 34. Also, low-molecular compounds like aluminum quinolate or metal chelate complexes are basis materials for OLED's.

Another alternative to the light emitting diode materials mentioned above are carbon nano tube structures which also have turned out to be adapted for high-luminous light sources within the scope of latest research.

Light emitting diodes 30, 32, 34 are particularly light emitting diodes emitting in a spectrally narrow band, the spectral light emission characteristics of which are shown in FIG. 4. In FIG. 4, the intensity distribution I is shown in a diagram in dependency of the wave length λ of the emitted light.

The spectral distribution of the intensity of the light emitted by the first light emitting diode 30 is designated with $I_1$. First light emitting diode 30 has a maximal radiation power in the blue range (B) of the spectrum. The intensity curve of second light emitting diode 32 is designated with $I_2$, the maximal radiation power of which being in the green range (G). The spectral intensity curve of third light emitting diode 34 is shown by $I_3$ the maximal radiation power of which being in the red range (R) of the spectrum.

In FIG. 2, the light emitting diode arrangement with the light emitting diodes 30, 32 and 34 is shown in an enlarged manner.

Light emitting diodes 30, 32 and 34 are arranged in a row in longitudinal direction of endoscope 10. Light emitting diodes 30, 32 and 34 are herein such oriented that their main radiation direction extends transversely with respect to the longitudinal direction of endoscope 10, as is indicated by arrows 38.

According to FIG. 1 and 2, illuminating system 26 of endoscope 10 further comprises an optical waveguide 40 that is formed of a glass fiber bundle. Optical waveguide 40 extends from the distal end of shaft 12 until approximately the level of first light emitting diode 30.

Light coupling means 42 are provided for coupling the light emitted by light emitting diodes 30, 32 and 34 into optical waveguide 40. Light coupling means 42 are formed by beam splitters, wherein a first beam splitter 44 is assigned to first light emitting diode 30, a second beam splitter 46 is assigned to second light emitting diode 32, and a third beam splitter 48 is assigned to third light emitting diode 34. Each of beam splitters 44, 46 and 48 comprises an at least partly reflecting layer, namely, first beam splitter 44 comprises an at least partly reflecting layer 50, second beam splitter 46 an at least partly reflecting layer 52 and third beam splitter 48 an at least partly reflecting layer 54.

The reflection and transmission characteristics in dependency of the light wave length of at least partly reflecting layers 50 and 52 of beam splitters 44 and 46 are also shown in FIG. 4.

To this end, the transmissivity T is shown in dependency of the wave length λ.

The transmission curve of the at least partly reflecting layer 50 of first beam splitter 44 is designated with $T_1$. As can be seen from FIG. 4, the transmissivity $T_1$, of at least partly reflecting layer 50 of first beam splitter 44 is 0 in the blue region, i.e. light in the blue region is completely reflected by at least partly reflecting layer 50. This means that the light emitted by first light emitting diode 30 in the blue region is coupled into the proximal end of optical waveguide 40 by beam splitter 44.

However, the transmissivity $T_1$ of the at least partly reflecting layer 50 of first beam splitter 44 in the green range and in the red range is 100%, i.e. light in the green range and the red range is completely let through by at least partly reflecting layer 50.

The transmissivity $T_2$ of at least partly reflecting layer 52 of second beam splitter 46 is 0 due to the transmission curve $T_2$ in the green and the blue range, i.e. light emitted by second light emitting diode 32 in the green range is reflected to 100% by beam splitter 46. As first beam splitter 44 is completely permeable in the green range, the light emitted by second light emitting diode 32 is also coupled in the green range into the proximal end of optical waveguide 40.

At least partly reflecting layer 52 of second beam splitter 46 is, however, permeable for light to 100% in the red range.

At least partly reflecting layer 54 of third beam splitter 48 is reflecting for light to 100% in the red range. The light emitted by third light emitting diode 34 in the red region is, thus, reflected by third beam splitter 48 and coupled into the proximal end of optical waveguide 40 due to the transmissivity of first and second beam splitter 44 and 46 in the red region.

The coupling direction for the light respectively emitted by first light emitting diode 30, second light emitting diode 32 and third light emitting diode 34 is indicated with arrows 56.

Due to the kind described above of coupling the light emitted by light emitting diodes 30, 32 and 34 into optical waveguide 40, an additive mixture of the light emitted by light emitting diodes 30, 32 and 34 takes place, so that correspondingly mixed light emerges from illuminating system 26, i.e. from optical waveguide 40 at the distal end of shaft 12 of endoscope 10, if light of at least two of light emitting diodes 30, 32, 34 is coupled into optical waveguide 40. In the case of the light emitting diode arrangement described above with blue luminous light emitting diode 30, green luminous light emitting diode 32 and red luminous light emitting diode 34, thus, with a corresponding mixture, white light of high intensity can be generated.

White light, however, can already be attained with merely two light emitting diodes instead of a light emitting diode arrangement with three light emitting diodes as described above, if the one light emitting diode emits light in a spectral region and the other light emitting diode emits light in a spectral region complementary to the other spectral region.

Modulations in color and/or intensity can be performed with the light emitting diode arrangement described above with three light emitting diodes in the blue, green and red frequency spectrum and with a corresponding driving of individual light emitting diodes 30, 32 and 34 in order to achieve an optimization of the light that emits at the distal end of optical waveguide 40 with respect to the faithfulness or the intensity of the color.

Light emitting diodes 30, 32, 34 may be driven in a pulsed manner or in a continuous manner. Light emitting diodes 30, 32 and 34 may herein also be driven in different manners in order to perform the modulation in color or intensity, whereby not only white light, but also colored light of a desired color may be generated.

For light emitting diodes 30, 32 and 34, current lines 58, 60 and 62 are schematically shown that are connected with a corresponding drive circuit and a current supply. The drive circuit and the current supply which are not shown in the figures are preferably also integrated in endoscope 10, so that endoscope 10 can be operated autonomously.

Beam splitters 44, 46 and 48 are adapted to the active cross section of optical waveguide 40 with respect to their cross sections, so that an optimal coupling in of the light emitted by light emitting diodes 30, 32 and 34 takes place that covers the whole active cross section of optical waveguide 40.

Furthermore, an element 64 for beam focusing is assigned for each of light emitting diodes 30, 32 and 34.

The arrangement of light emitting diodes 30, 32 and 34 is, further, detachable from the arrangement of beam splitters 44, 46 and 48, as is indicated by a line 66 in FIG. 2. Light emitting diodes 30, 32 and 34 can, thus, be exchanged against other light emitting diodes according to one's needs.

In FIG. 3, another embodiment of illuminating system 70 is shown that comprises an optical waveguide 72 comparable to optical waveguide 40. Illuminating system 70 comprises a multiple arrangement of three light emitting diodes 74, 76 and 78, respectively, and of three beam splitters 80, 82 and 84, wherein light emitting diodes 74, 76 and 78 and beam splitters 80, 82 and 84 are configured correspondingly to light emitting diodes 30, 32, 34 and beam splitters 44, 46 and 48.

Altogether, three such arrangements of light emitting diodes 74, 76 and 78 and beam splitters 80, 82 and 84 are provided for illuminating system 70.

A further optical waveguide 86 is assigned to each of arrangements of light emitting diodes 74, 76 and 78 and beam splitters 80, 82 and 84, into which optical waveguide the light emitted by light emitting diodes 74, 76 and 78 is additively coupled. Three further optical waveguides 86 then join each other to form a common optical waveguide end 88, emerging from which the light is coupled into optical waveguide 72.

Optical waveguide end 88 with the light emitting diodes/beam splitter arrangements can be coupled off optical waveguide 72, as is indicated with a line 90.

Figure 5:
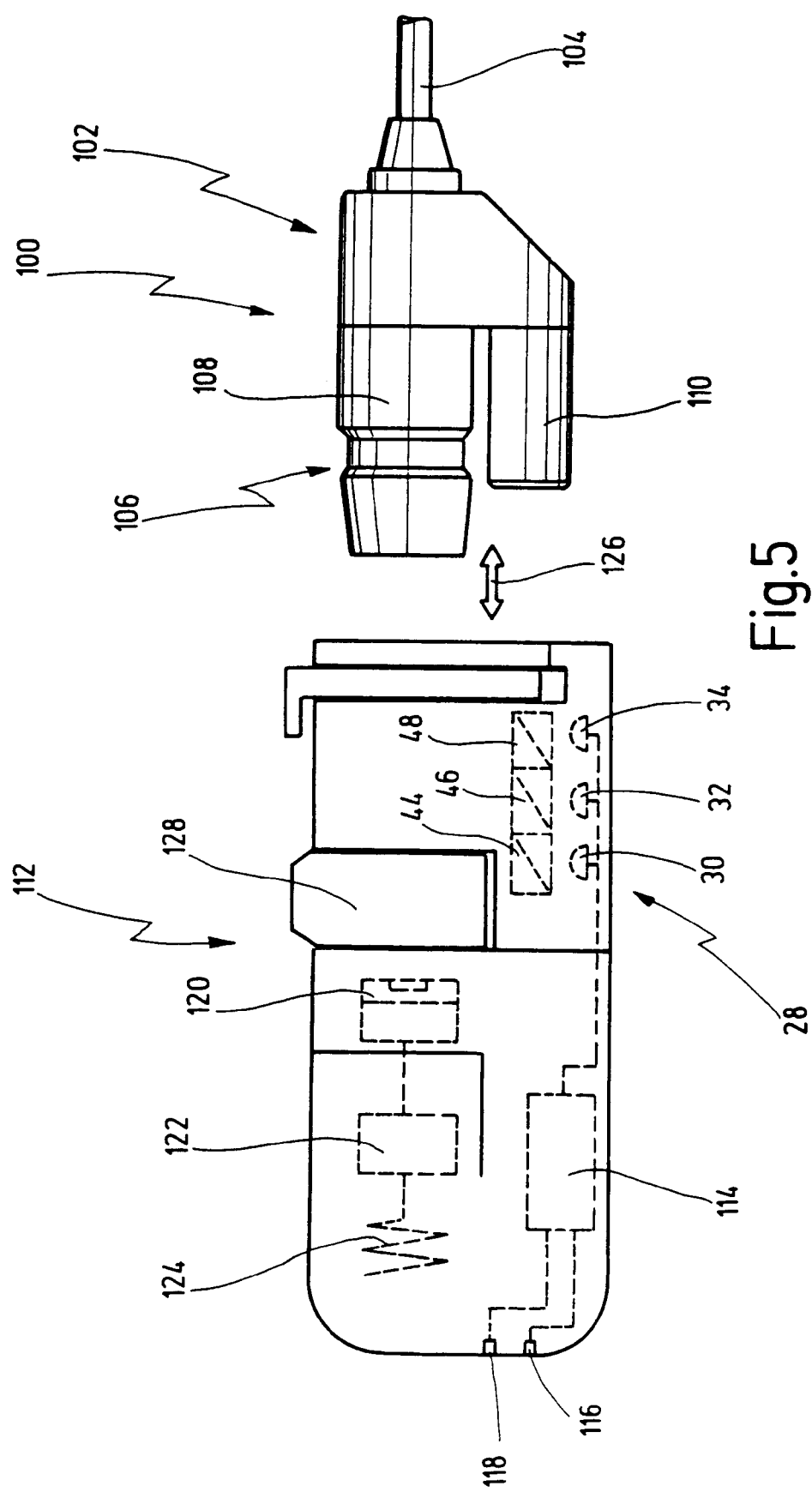
FIG. 5 shows a sectional view of an endoscope with a coupling unit for light and image transmitting connection of an endoscope with a camera module.

Finally, another embodiment of an endoscope 100 is shown in FIG. 5 that can be assembled of two parts. A first part 102 comprises an endoscope shaft 104, at the proximal end of which a plug coupling 106 is arranged. Plug coupling 106 comprises a first pin 108, in which the proximal-sided end of the imaging system is received, and a second pin 110, in which the proximal end of the illuminating system is arranged that comprises an optical waveguide.

Light source 28, in its turn, which is labeled with the reference numeral 28 which comprises e.g. light emitting diodes 30, 32, 34 already mentioned before is now arranged in a coupling unit 112 that is detachable from endoscope 100.

Coupling unit 112 corresponds to the coupling unit described in DE 197 15 510 A1 with respect to the configuration of the coupling mechanism, so reference is made to said description with respect to that.

The features modified in comparison to the coupling unit described therein are drawn with interrupted lines in FIG. 5, such as light emitting diodes 30, 32 and 34, for example. As was described with reference to the previous embodiments, again, coupling means are assigned in the form of beam splitters 44, 46 and 48 to each light emitting diode 30, 32 and 34. As current supply for light emitting diodes 30, 32 and 34, a battery or a rechargeable battery 114 is arranged in coupling unit 112. In the case that a rechargeable battery is provided, further, plug contacts 116 and 118 are provided at the proximal end of the housing of coupling unit 112, via which plug contacts coupling unit 112 can be connected onto a suitable battery charging device in order to charge rechargeable battery 114.

Coupling unit 112 further comprises a camera module 120 with a suitable imager chip which transforms the light transmitted by the image transmission system of endoscope 100 via pin 108 into coupling unit 112 into corresponding electric signals. Camera module 120 is further connected to a sender 122 via which the signals created by camera module 120 can be radiated via a suitable antenna 124 in a wireless manner, which signals can be received by a corresponding receiver and can be shown on a video screen as real images.

Coupling unit 112 and endoscope 100 are plugged together in use according to a double arrow 126, as is described in DE 197 15 510 A1. In the plugged state, beam splitters 44, 46 and 48 lie on the level of pin 110 and camera module 120 lies on the level of pin 108.

A focusing unit 128 is correspondingly added to camera module 120.

In comparison to the coupling unit described in DE 197 15 510 A1, coupling unit 112 requires neither a connection for an external light conducting cable nor a connection for a electric cable for transmitting the signals from camera module 120 onto a video unit. Rather, coupling unit 112 is completely autonomous and free of disturbing connecting cables.

What is claimed is:

1. An endoscope, comprising:
   a shaft having a distal end and a proximal end;
   an imaging system arranged in said shaft;
   a light source including at least two light emitting diodes for emitting light in different spectral ranges; and
   an illuminating system including an optical waveguide and light coupling means for coupling in said light emitted by said at least two light emitting diodes into said optical waveguide and thereby allowing said light to emerge at said distal end of said shaft, said light coupling means including plural beam splitters each having at least partly reflecting layers and being assigned to each corresponding light emitting diode;
   wherein said light source comprises at least two light emitting diodes and said light coupling means are arranged at a proximal end of said optical waveguide, and wherein said light of said at least two light emitting diodes emerges spectrally addictively mixed from said illuminating system.

2. The endoscope of claim 1, wherein said at least two light emitting diodes emit light in spectral images that are spectrally complementary to each other.

3. The endoscope of claim 1, wherein said light source comprises at least three light emitting diodes which emit light in the blue, green, and red spectral range.

4. The endoscope of claim 1, wherein said at least two light emitting diodes comprise a spectrally narrow band radiation characteristic and a high light intensity.

5. The endoscope of claim 1, wherein said beam splitters are arranged in a row in axial extension of said optical waveguide, and wherein each beam splitter is reflecting in the spectral range of said light emitted by said assigned light emitting diode and permeable in the spectral range(s) of said light emitted by said light emitting diode(s) disposed behind.

6. The endoscope of claim 5, wherein said cross section of each beam splitter corresponds to an active cross section of said optical waveguide.

7. The endoscope of claim 1, wherein said illuminating system comprises a first optical waveguide, and wherein light coupling means are provided for coupling in said light emitted by said at least two light emitting diodes into said first optical waveguide, and wherein a plurality of arrangements of several light emitting diodes and light coupling means is provided, and wherein a further optical waveguide is assigned to each of these arrangements, and wherein said further optical waveguides are coupled with said first optical waveguide.

8. The endoscope of claim 1, wherein said at least two light emitting diodes are arranged in said endoscope.

9. The endoscope of claim 8, wherein said at least two light emitting diodes are detachable from said endoscope.

10. The endoscope of claim 1, wherein said at least two light emitting diodes can be driven in pulsed or continuous manner.

11. The endoscope of claim 10, wherein said light emitting diodes having different radiation spectrums can be driven differently.

12. The endoscope of claim 1, wherein a drive circuit for said at least two light emitting diodes is arranged in said endoscope.

13. The endoscope of claim 1, wherein a current supply for said at least two light emitting diodes is arranged in said endoscope.

14. The endoscope of claim 13, wherein said current supply is, together with said at least two light emitting diodes, detachable as a unit from said endoscope.

15. The endoscope of claim 1, wherein said at least two light emitting diodes are arranged in a coupling unit detachable from said endoscope for light and image transmitting connection of said endoscope with a camera module.

16. The endoscope of claim 15, wherein in said coupling unit a sender is arranged for wireless transmission of a video image picked up by said camera module.

17. The endoscope of claim 1, wherein said at least two light emitting diodes are arranged in a coupling unit detachable from said endoscope for light and image transmitting connection of said endoscope with a camera module and wherein a current supply is arranged for said at least two light emitting diodes in said coupling unit.

* * * * *